US00PP28866P2

(12) United States Plant Patent
Winner

(10) Patent No.: US PP28,866 P2
(45) Date of Patent: Jan. 9, 2018

(54) ***COREOPSIS* PLANT NAMED 'BALUPTEAMED'**

(50) Latin Name: ***Coreopsis* hybrid**
Varietal Denomination: Balupteamed

(71) Applicant: Ball Horticultural Company, West Chicago, IL (US)

(72) Inventor: Blair Winner, Ventura, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/330,412

(22) Filed: Sep. 16, 2016

(51) Int. Cl.
*A01H 5/02* (2006.01)

(52) U.S. Cl.
USPC ..... Plt./417

(58) Field of Classification Search
USPC ..... Plt./417
CPC ..... A01H 5/025; A01H 5/02; A01H 5/00
See application file for complete search history.

(56) References Cited

U.S. PATENT DOCUMENTS

PP20,412 P2 * 10/2009 Probst ..... A01H 5/025 Plt./417

OTHER PUBLICATIONS

Ball Seed 2017 Plant Information *Coreopsis* Uptick Cream & Red, retrieved on Sep. 12, 2017, retrieved from the Internet at http://www.ballseed.com/PlantInfo/?phid=018907658028294 2 pp. (Year: 2017).*

Greenhouse Management 2016 UpTick *Coreopsis,* retrieved on Sep. 11, 2017, retrieved from the Internet at http://www.greenhousemag.com/article/uptick--coreopsis/ 5 pp. (Year: 2016).*

* cited by examiner

*Primary Examiner* — June Hwu
(74) *Attorney, Agent, or Firm* — Audrey Charles

(57) ABSTRACT

A new and distinct cultivar of *Coreopsis* plant named 'Balupteamed', characterized by its single-type, creamy-yellow colored inflorescences having a medium-sized, burgundy-red colored eye zone, medium green-colored foliage, and vigorous, semi-upright growth habit, is disclosed.

1 Drawing Sheet

Latin name of genus and species of plant claimed: *Coreopsis* hybrid.

Variety denomination: 'Balupteamed'.

BACKGROUND OF THE INVENTION

The present invention relates to a new and distinct cultivar of *Coreopsis* plant botanically known as *Coreopsis* hybrid and hereinafter referred to by the cultivar name 'Balupteamed'.

The new cultivar originated in a controlled breeding program in Santa Paula, Calif. during October 2011. The objective of the breeding program was the development of *Coreopsis* cultivars having large inflorescences, substantially continuous blooming throughout the summer, and mounded growth habits.

The new *Coreopsis* cultivar is the result of open-pollination. The female (seed) parent of the new cultivar is Big Bang 'Redshift', U.S. Plant Pat. No. 20,412, characterized by its single-type, light yellow-colored inflorescences having a burgundy-red colored eye zone that extends when temperatures cool, dark green-colored foliage, and vigorous, upright growth habit. The male (pollen) parent of the new cultivar is unknown. The new cultivar was discovered and selected as a single flowering plant within the progeny of the above stated open-pollination during May 2012 in a controlled environment in Santa Paula, Calif.

Asexual reproduction of the new cultivar by terminal stem cuttings since May 2012 in Santa Paula, Calif. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balupteamed' as a new and distinct cultivar of *Coreopsis* plant:

1. Single-type, creamy-yellow colored inflorescences having a medium-sized, burgundy-red colored eye zone;
2. Medium green-colored foliage; and
3. Vigorous, semi-upright growth habit.

Plants of the new cultivar differ from plants of the female parent primarily in having inflorescences with a more distinct eye zone, particularly during the cool growing season, and in having a shorter and narrower growth habit. In the population of potential male parents there was none having all the characteristics of the plant of the new cultivar.

Of the many commercially available *Coreopsis* cultivars, the most similar in comparison to the new cultivar is the *Coreopsis* cultivar BIG BANG 'Star Cluster', U.S. Plant Pat. No. 23,035. However, in comparison, plants of the new cultivar differ from plants of 'Star Cluster' in at least the following characteristics:

1. Plants of the new cultivar have a ray floret color different from plants of 'Star Cluster';

2. Plants of the new cultivar have larger leaves than plants of 'Star Cluster'; and
3. Plants of the new cultivar have smaller diameter inflorescences than plants of 'Star Cluster'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balupteamed'. The plants were approximately 17 weeks old and grown in 1.7 gallon containers. Plants were finished outdoors for 7 weeks in West Chicago, Ill. Plants were given two pinches prior to transplant.

DETAILED BOTANICAL DESCRIPTION

Figure 1:
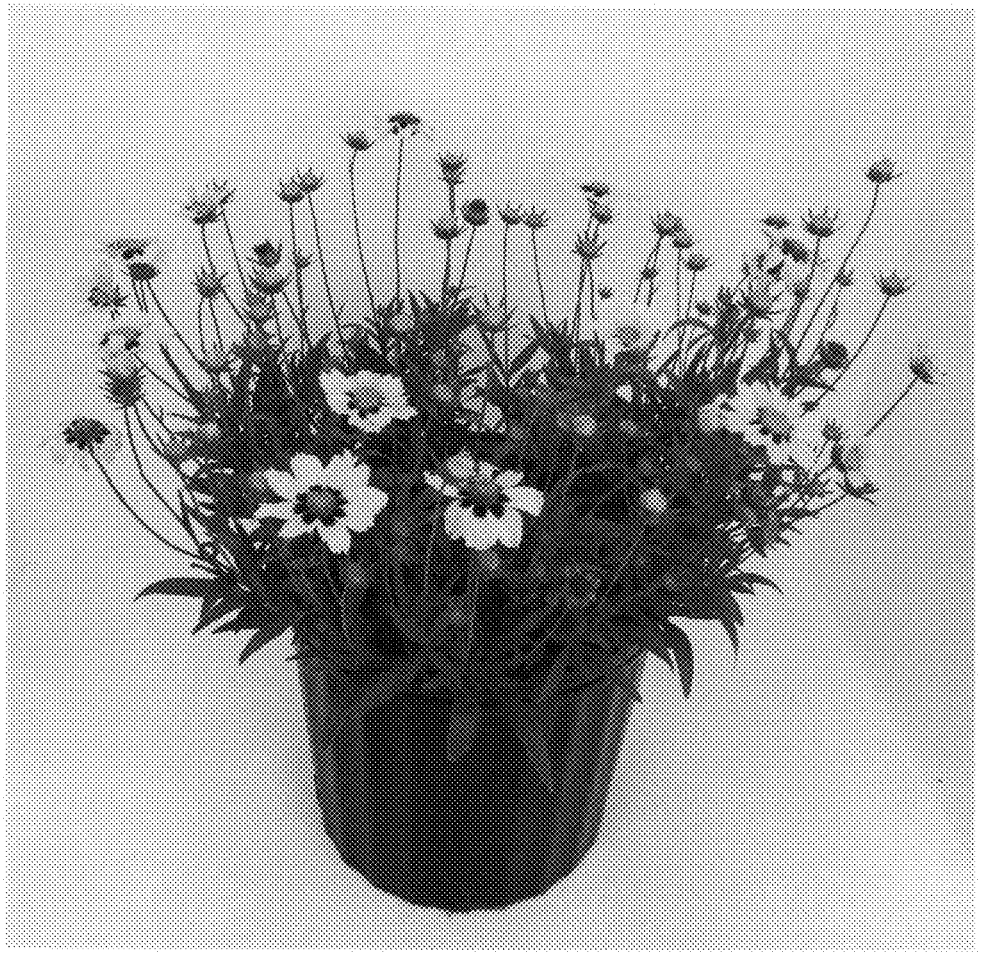
FIG. 1 illustrates a side view of the overall growth and flowering habit of 'Balupteamed'.
Figure 2:
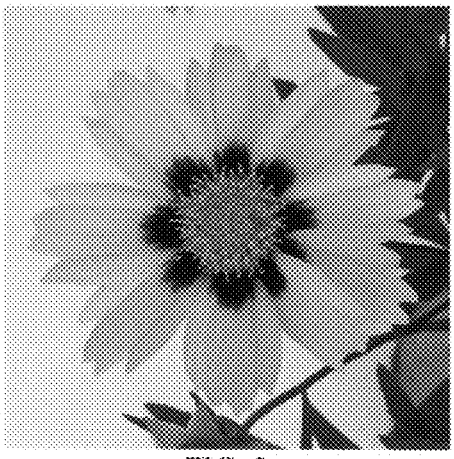
FIG. 2 illustrates a close-up view of an inflorescence of 'Balupteamed'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2016 under natural light conditions in West Chicago, Ill.

The following descriptions and measurements describe plants produced from cuttings from stock plants and grown under conditions comparable to those used in commercial practice. The plants were grown utilizing a soilless growth medium in 1.7 gallon containers for approximately 17 weeks. Plants were given two pinches prior to transplant. For approximately 8 weeks after transplant, greenhouse temperatures were maintained at approximately 60° F. (15.6° C.) during the day and approximately 55° F. (12.8° C.) during the night. For the final 7 weeks, plants were grown outside in West Chicago, Ill. No supplemental lighting was provided. Measurements and numerical values represent averages of typical plants.

Botanical classification: *Coreopsis* hybrid cultivar Balupteamed.

Parentage:

*Female parent.*—Big Bang 'Redshift', U.S. Plant Pat. No. 20,412.

*Male parent.*—Unknown.

Propagation:

*Type cutting.*—Terminal stem.

*Time to initiate roots.*—Approximately 10 to 12 days at 70° F. (21° C.).

*Time to produce a rooted cutting.*—Approximately 5 to 6 weeks at 70° F. (21° C.).

*Root description.*—Fibrous, thin, white in color.

*Rooting habit.*—Freely branching, dense.

Plant description:

*Commercial crop time.*—Approximately 10 to 12 weeks from a rooted cutting to finish in a one-gallon container.

*Growth habit and general appearance.*—Herbaceous perennial, vigorous, semi-upright growth habit.

*Hardiness.*—USDA zones 5 to 9.

*Size.*—Height from soil level to top of plant plane: Approximately 29.0 cm. Width: Approximately 33.0 cm.

*Branching habit.*—Freely branching, pinching improves basal branching. Quantity of lateral branches per plant: Approximately 12 main branches each having approximately 4 lateral branches.

*Main branches.*—Strength: Moderately strong. Length to base of peduncle: Approximately 11.0 cm. Diameter: Approximately 3.0 mm. Length of central internode: Approximately 4.0 cm. Texture: Slightly glossy, glabrous. Color of young and mature stems: 144A.

Foliage description:

*General description.*—Quantity of leaves per main branch: Approximately 6. Type: Simple and trifoliate. Fragrance: None. Arrangement: Opposite. Aspect: Petiole is acute angle to stem; blade is somewhat perpendicular to stem. Shape of leaf and leaflet: Elliptic. Margin of leaf and leaflet: Entire. Apex of leaf and leaflet: Acute. Base of leaf and leaflet: Attenuate, simple leaf sessile. Venation pattern: Pinnate.

*Simple leaf.*—Length: Approximately 8.0 cm. Width: Approximately 1.5 cm. Texture of upper and lower surfaces: Sparsely pubescent. Color of upper surface when first and fully open: 137B with indistinguishable venation except for midvein of 146B. Color of lower surface when first and fully open: Closest to 138B with indistinguishable venation except for midvein of 146B.

*Mature trifoliate leaf.*—Length of mature trifoliate leaf: Approximately 8.0 cm. Width of mature trifoliate leaf: Approximately 6.5 cm. Length of terminal leaflet: Approximately 7.5 cm. Width of terminal leaflet: Approximately 1.5 cm. Length of lateral leaflet: Approximately 3.5 cm. Width of lateral leaflet: Approximately 8.0 mm. Texture of upper and lower surfaces: Sparsely pubescent. Color of upper surface when first and fully open: 137B with indistinguishable venation except for midvein of 146B. Color of lower surface when first and fully open: Closest to 138B with indistinguishable venation except for midvein of 146B. Length of petiole of mature trifoliate leaf: Approximately 1.0 cm. Diameter of petiole of mature trifoliate leaf: Approximately 3.0 mm. Texture of petiole of mature trifoliate leaf: Sparsely pubescent. Color of upper and lower surfaces of petiole of mature trifoliate leaf: 146B.

Flowering description:

*Flowering habit.*—'Balupteamed' is freely flowering under outdoor growing conditions with substantially continuous blooming from spring through autumn.

*Lastingness of individual inflorescence on the plant.*—Approximately 7 to 10 days.

Inflorescence description:

*General description.*—Type: Daisy-type composite, actinomorphic. Persistent. Shape: Round. Aspect: Erect. Arrangement: Terminal capitulum, positioned above and below the foliage. Quantity per plant:

Approximately 17. Diameter: Approximately 4.8 cm. Depth: Approximately 2.0 cm. Fragrance: Slightly acrid.

*Peduncle.*—Strength: Strong. Aspect: Erect. Length: Approximately 14 cm to 16.5 cm. Diameter: Approximately 2.0 mm. Texture: Glabrous, slightly glossy. Color: Between 144A and 144B.

*Bud.*—Rate of opening: Generally takes 4 to 5 days for bud to progress from first color to fully open inflorescence. Quantity per plant: Approximately 65.

*Bud just before opening.*—Shape: Obovoid. Diameter: Approximately 1.0 cm. Depth: Approximately 9.0 mm. Color: 151A and 152C.

*Ray florets.*—Quantity per inflorescence: Approximately 8 to 9. Arrangement: In a single whorl, slightly imbricate. Aspect: Flattened. Shape: Obovate to oblong. Margin: Entire. Apex: Incised. Base: Rounded. Length: Approximately 2.3 cm. Width: Approximately 1.2 cm. Texture of upper and lower surfaces: Glabrous, abaxially ribbed. Color of upper surface when first open: 4A with base of 187A. Color of lower surface when first open: 4B with streaks of 187A at base and venation of 4A. Color of upper surface when fully open: 4B with base of 187A. Color of lower surface when fully open: 4C with streaks of 187A at base and venation of 4B.

*Disc florets.*—Quantity per inflorescence: Approximately 120. Arrangement: Massed in center of inflorescence. Shape: Tubular, approximately lower 90% fused. Margin: Entire. Apex: Five acute tips. Base: Fused. Length: Approximately 1.0 cm. Diameter at tube opening: Approximately 2.0 mm. Diameter at base: Approximately 1.0 mm. Texture of outer surface: Glabrous. Texture of inner surface: Glabrous with glandular pubescence on tips. Color of upper or inner surface when first and fully open: Closest to 154D, translucent with tips of 17A. Color of lower or outer surface when fully open: Closest to 154D, translucent with tips of 17B.

*Disc.*—Diameter: Approximately 1.3 cm. Depth: Approximately 5.0 mm.

*Receptacle.*—Shape: Dome. Height: Approximately 2.0 mm. Diameter at base: Approximately 4.0 mm. Color: 145D.

*Phyllaries.*—Quantity per inflorescence Approximately 16. Arrangement: In two equally divided whorls. Base of inner whorl fused into cup-shaped base surrounding receptacle, non-imbricate, held close to ray florets.

*Outer phyllaries.*—Shape: Lanceolate. Margin: Entire, ciliate. Apex: Acute. Base: Truncate. Length: Approximately 8.0 mm. Width: Approximately 2.0 mm. Texture of upper and lower surfaces: Glabrous, glossy. Color of upper and lower surfaces: 137B.

*Inner phyllaries.*—Shape of free portion: Ovate. Margin: Entire. Apex: Acute. Base: Fused. Length: Approximately 1.0 cm. Width: Approximately 5.0 mm. Texture of upper and lower surfaces: Glabrous. Color of upper and lower surfaces: 152D with cup-shaped portion of closest to 144B.

*Reproductive organs.*—Androecium: Present on disc florets only. Stamen quantity: 5. Stamen length: Approximately 6.0 mm. Filament length: Approximately 3.0 mm. Filament color: 154D. Anther shape: Oblong, basifixed. Anther length: Approximately 3.0 mm. Anther color: 154D, translucent, slightly tinted with 183A. Pollen amount: Abundant. Pollen color: 17A. Gynoecium: Present on disc florets only. Pistil quantity: 1 per floret. Pistil length: Approximately 1.0 cm. Stigma shape: 2-branched. Stigma length: Each branch approximately 1.0 mm. Stigma color: 17B. Style length: Approximately 8.0 mm. Style color: 154D. Ovary length: Approximately 2.0 mm. Ovary color: 145D.

Seed and fruit production: Neither seed nor fruit production has been observed.

Disease and pest resistance: Resistance to pathogens and pests common to *Coreopsis* has not been observed.

What is claimed is:

1. A new and distinct cultivar of *Coreopsis* plant named 'Balupteamed' substantially as herein illustrated and described.

* * * * *